US012263143B2

(12) United States Patent
Hill Mongabure et al.

(10) Patent No.: US 12,263,143 B2
(45) Date of Patent: Apr. 1, 2025

(54) IONIC CHANNEL MODULATION AS A METHOD FOR TREATING TUMORS THROUGH INFLAMMASOME ACTIVATION

(71) Applicants: Institut Pasteur de Montevideo, Montevideo (UY); University of the Republic, Montevideo (UY)

(72) Inventors: Marcelo Hill Mongabure, Canelones (UY); Sofia Russo Rossi, Montevideo (UY); Mercedes Segovia Duarte, Canelones (UY); María Inés Varela Vega, Montevideo (UY); Pablo Oppezzo Llorens, Canelones (UY)

(73) Assignees: Institut Pasteur de Montevideo, Montevideo (UY); University of the Republic, Montevideo (UY)

( * ) Notice: Subject to any disclaimer, the term of this patent is extended or adjusted under 35 U.S.C. 154(b) by 715 days.

(21) Appl. No.: 17/513,232

(22) Filed: Oct. 28, 2021

(65) Prior Publication Data
US 2022/0184004 A1 Jun. 16, 2022

Related U.S. Application Data

(63) Continuation-in-part of application No. PCT/IL2020/050475, filed on Apr. 28, 2020.

(60) Provisional application No. 62/839,693, filed on Apr. 28, 2019.

(51) Int. Cl.
| | | |
|---|---|---|
| A61K 31/138 | (2006.01) | |
| A61K 31/166 | (2006.01) | |
| A61K 31/167 | (2006.01) | |
| A61K 31/4166 | (2006.01) | |
| A61K 31/496 | (2006.01) | |
| A61K 31/55 | (2006.01) | |
| A61P 35/00 | (2006.01) | |
| C07K 16/28 | (2006.01) | |

(52) U.S. Cl.
CPC .......... *A61K 31/138* (2013.01); *A61K 31/166* (2013.01); *A61K 31/167* (2013.01); *A61K 31/4166* (2013.01); *A61K 31/496* (2013.01); *A61K 31/55* (2013.01); *A61P 35/00* (2018.01); *C07K 16/2818* (2013.01); *C07K 16/2827* (2013.01)

(58) Field of Classification Search
CPC .. A61K 31/138; A61K 31/166; A61K 31/167; A61K 31/4166; A61K 31/55; A61P 35/00; C07K 16/2818; C07K 16/2827
See application file for complete search history.

(56) References Cited

U.S. PATENT DOCUMENTS

2002/0156016 A1* 10/2002 Minuk ................... A61K 31/55
514/17.4
2017/0327567 A1 11/2017 Skokos et al.

FOREIGN PATENT DOCUMENTS

| WO | WO-2011131472 A1 * | 10/2011 | ............. A61K 31/05 |
|---|---|---|---|
| WO | 2015059463 A2 | 4/2015 | |
| WO | 2018203262 A1 | 11/2018 | |
| WO | 2021173916 A1 | 9/2021 | |

OTHER PUBLICATIONS

Irizarry-Caro et al, Drugs Implicated in Systemic Autoimmunity Modulate Neutrophil Extracellular Trap Formation, Arthritis Rheumatol. Mar. 2018; 70 (3): 468-474, doi: 10.1002/art.40372 (Year: 2018).*
Irizarry-Caro, "Drugs Implicated in Systemic Autoimmunity Modulate Neutrophil Extracellular Trap Formation", Arthritis and Rheumatology, Mar. 2018' 70 (3): 468-474 (Year: 2018).*
Ji et al. (2016). "Aconitine induces cell apoptosis in human pancreatic cancer via NF-κB signaling pathway"; Department of Laboratory Medicine, Hospital of Traditional Chinese Medicine of Lishui City, Lishui, Zhejiang, China; European Review for Medical and Pharmacological Sciences; 2016; 20: 4955-4964; Retrieved Nov. 22, 2021; PMID: 27981537.
Leng, Tiandong et al. (2017). "Lidocaine suppresses glioma cell proliferation by inhibiting TRPM7 channels." International Journal of Physiology, Pathophysiology and Pharmacology vol. 9 (2), pp. 8-15. Retrieved Nov. 22, 2021; PMID: 28533887.
Segura-Pacheco et al. (2003). "Reactivation of tumor suppressor genes by the cardiovascular drugs hydralazine and procainamide and their potential use in cancer therapy". Clin. Cancer Res. May 2003;9(5):1596-603. Retrieved Nov. 22, 2021 from: https://pubmed.ncbi.nlm.nih.gov/12738711/; PMID: 12738711.
Zheng, Wei-Bin et al. (2017). "Propafenone suppresses esophageal cancer proliferation through inducing mitochondrial dysfunction." American journal of cancer research vol. 7,11 2245-2256. Nov. 1, 2017 Retrieved Nov. 22, 2021 from: https://www.ncbi.nlm.nih.gov/pmc/articles/PMC5714753/.
Abdullah, A. et al. (2015). A plant alkaloid, veratridine, potentiates cancer chemosensitivity by UBXN2A-dependent inhibition of an oncoprotein, mortalin-2. Oncotarget. Sep. 15, 2015;6(27):23561-81. doi: 10.18632/oncotarget.4452. Retrieved Nov. 22, 2021 from: https://pubmed.ncbi.nlm.nih.gov/26188124/; PMID: 26188124; PMCID: PMC4695137.
Nelson, M. et al. (2015). "The sodium channel-blocking antiepileptic drug phenytoin inhibits breast tumour growth and metastasis". Mol Cancer. Jan. 27, 2015;14(1):13. doi: 10.1186/s12943-014-0277-x. Retrieved Nov. 22, 2021 from: https://pubmed.ncbi.nlm.nih.gov/25623198/; PMID: 25623198; PMCID: PMC4320839.
Segovia et al. (2020). Role of inflammasome activation in tumor immunity triggered by immune checkpoint blockers. Clinical and Experimental Immunology, vol. 200, Issue 2, May 2020, pp. 155-162. Retrieved Nov. 22, 2021; https://doi.org/10.1111/cei.13433.

(Continued)

*Primary Examiner* — Noble E Jarrell
*Assistant Examiner* — Phillip Matthew Rzeczycki
(74) *Attorney, Agent, or Firm* — The Roy Gross Law Firm, LLC; Roy Gross (57) ABSTRACT

The invention presents use of ion channel modulator to manipulate expression of the Tmem176b gene, also known as TORID (TOlerance Related and InduceD), to treat tumors.

2 Claims, 10 Drawing Sheets

(56) References Cited

OTHER PUBLICATIONS

Segovia et al. (2019). Targeting TMEM176B Enhances Antitumor Immunity and Augments the Efficacy of Immune Checkpoint Blockers by Unleashing Inflammasome Activation. Cancer Cell. May 13, 2019;35(5):767-781.e6. doi: 10.1016/j.ccell.2019.04.003. Retrieved Nov. 22, 2021 from: https://onlinelibrary.wiley.com/share/VC6UXUFNEMFJNEZ8FBHD?target=10.1111/cei.13433.

PCT International Search Report for International Application No. PCT/IL2020/050475, mailed Jun. 16, 2020, 7pp.

PCT Written Opinion for International Application No. PCT/IL2020/050475, mailed Jun. 17, 2020, 10pp.

PCT International Preliminary Report on Patentability for International Application No. PCT/IL2020/050475, completed Jun. 17, 2021, 6pp.

Sharma, P. and J. P. Allison, "Immune checkpoint targeting in cancer therapy: toward combination strategies with curative potential." Cell 161(2): 205-214(2015).

Topalian, S. L., C. G. Drake and D. M. Pardoll, "Immune checkpoint blockade: a common denominator approach to cancer therapy." Cancer Cell 27(4): 450-461(2015).

Baumeister, S. H., G. J. Freeman, G. Dranoff and A. H. Sharpe, "Coinhibitory Pathways in Immunotherapy for Cancer." Annu Rev Immunol 34: 539-573 (2016).

Twyman-Saint , Victor C. et al. Radiation and dual checkpoint blockade activates non-redundant immune mechanisms in cancer. Nature. Apr. 16, 2015;520(7547):373-7. doi: 10.1038/nature 14292. Epub Mar. 9, 2015. PMID: 25754329; PMCID: PMC4401634.

Extended European Search Report for European Patent Application No. 20798337.6, dated May 27, 2022, 14pp.

\* cited by examiner

SDZ-201106

Veratridine

Phenytoin

FIG 3B

Aconitine

Lidocaine

Procainamide

Propafenone

Continued FIG 3B

IONIC CHANNEL MODULATION AS A METHOD FOR TREATING TUMORS THROUGH INFLAMMASOME ACTIVATION

REFERENCE TO RELATED PUBLICATIONS

This application is a Continuation-in-Part of U.S. National Phase entry of PCT (International) Pat. Appl. No. PCT/IL2020/050475, filed on Apr. 28, 2020, and which claims priority from U.S. Provisional Pat. Appl. No. 62/839,693, filed on Apr. 28, 2019. All of these applications are incorporated by reference in their entirety.

FIELD OF THE INVENTION

The present invention pertains to ionic channel modulation as a method for treating tumors through inflammasome activation, use, and methods thereof.

BACKGROUND OF THE INVENTION

Manipulation of the immune system to trigger anti-tumoral immune responses has revolutionized the therapeutic approach of a variety of cancers, see Sharma, P. and J. P. Allison, "Immune checkpoint targeting in cancer therapy: toward combination strategies with curative potential." Cell 161(2): 205-214(2015); Topalian, S. L., C. G. Drake and D. M. Pardoll, "Immune checkpoint blockade: a common denominator approach to cancer therapy." Cancer Cell 27(4): 450-461(2015); and Baumeister, S. H., G. J. Freeman, G. Dranoff and A. H. Sharpe, "Coinhibitory Pathways in Immunotherapy for Cancer." Annu Rev Immunol 34: 539-573 (2016); all are incorporated herein as a reference.

Particularly, Immune Checkpoint Blockade has reach outstanding clinical results from immunotherapy, by unleashing the natural breaks on T cells that normally hold them to prevent autoimmune attack. However, only a minority of patients treated with these drugs experience substantial clinical benefit. Thus, the identification, characterization and manipulation of novel targets to promote anti-tumoral immune responses are necessary to overcome this resistance.

SUMMARY OF THE INVENTION

One object of the invention is to disclose a method for identifying at least one composition capable of improving the efficacy of an immune checkpoint blocker (a second therapeutic agent) to treat tumors, wherein said method comprises steps of assaying said at least one composition for both
  a. triggering inflammasome activation; and
  b. inhibiting TORID-dependent ion flux Another object of the invention is to disclose the method as defined above, wherein said one composition configured to trigger inflammasome activation and to inhibit TORID-dependent ion fluxes, is selected from a group consisting of Aconitine, Lidocaine, Procainamide, Propafenone and any combination thereof.

Another object of the invention is to disclose the method as defined above, wherein one or more second therapeutic agents are administrable either concurrently or sequentially to a patient in need.

Another object of the invention is to disclose the method as defined above, wherein said second therapeutic agent is selected from a group consisting of either an anti-CTLA4 antibody or an anti-PD-1/PD-L1 antibody; and any combination thereof.

One object of the invention is to disclose a therapeutic mixture of at least one composition, capable of improving the efficacy of one or more second therapeutic agents, wherein said composition is configured to trigger inflammasome activation and to inhibit TORID-dependent ion fluxes, further wherein said second therapeutic agent is selected from a group consisting of either an anti-CTLA4 antibody or an anti-PD-1/PD-L1 antibody; and any combination thereof. One object of the invention is to disclose use of ion channel modulator to manipulate expression of the Tmem176b gene, also known as TORID (TOlerance Related and InduceD), to treat tumors.

Another object of the invention is to disclose use as defined above, wherein the channel modulator are configured to inhibit TORID-dependent ion fluxes selected from a group consisting of Aconitine, Lidocaine, Procainamide, Propafenone, QX-314, SDZ201106, Veratridine and Phenytoin.

Another object of the invention is to disclose use as defined in any of the above wherein one or more second therapeutic agents are administrated either concurrently or sequentially to a patient in need.

Another object of the invention is to disclose use as defined in any of the above wherein the second therapeutic agent is selected from a group consisting of (a) either an anti-CTLA4 antibody or an anti-PD-1/PD-L1 antibody; (b) radiation therapy (c) a combination of both.

Another object of the invention is to disclose a method of inhibiting TORID to impair tumor growth comprising step(s) of exposing TORID to a pharmacologically active amount of an ion channel modulator.

Another object of the invention is to disclose a method as defined in any of the above wherein the channel modulator are configured to inhibit TORID-dependent ion fluxes selected from a group consisting of Aconitine, Lidocaine, Procainamide, Propafenone, QX-314, SDZ201106, Veratridine and Phenytoin.

Another object of the invention is to disclose a method as defined in any of the above wherein one or more second therapeutic agents are administrated either concurrently or sequentially to a patient in need.

Another object of the invention is to disclose a method as defined in any of the above wherein the second therapeutic agent is selected from a group consisting of (a) either an anti-CTLA4 antibody or an anti-PD-1/PD-L1 antibody; (b) radiation therapy (c) a combination of both.

Still another object of the invention is to disclose an ion channel modulator useful for inhibiting TORID to impair tumor growth selected from a group consisting of Aconitine, Lidocaine, Procainamide, Propafenone, QX-314, SDZ201106, Veratridine and Phenytoin.

Yet another object of the invention is to disclose therapeutic mixture of an ion channel modulator and one or more second therapeutic agents, wherein said ion channel modulator is selected from a group consisting of Aconitine, Lidocaine, Procainamide, Propafenone, QX-314, SDZ201106, Veratridine and Phenytoin and further wherein said second therapeutic agent is selected from a group consisting of (a) either an anti-CTLA4 antibody or an anti-PD-1/PD-L1 antibody; (b) radiation therapy; (c) a combination of both.

DETAILED DESCRIPTION OF THE INVENTION

The invention has been described using exemplary preferred embodiments. However, for those skilled in this field, the preferred embodiments can be easily adapted and modified to suit additional applications without departing from the spirit and scope of this invention. Thus, it is to be understood that the scope of the invention is not limited to the disclosed embodiments. On the contrary, it is intended to cover various modifications and similar arrangements based upon the same operating principle. The scope of the claims, therefore, should be accorded the broadest interpretations so as to encompass all such modifications and similar arrangements.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound to the present invention and a pharmaceutically acceptable carrier. A composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment.

"Administering" when used in conjunction with a therapeutic means to administer a therapeutic directly to a subject, whereby the agent positively impacts the target. "Administering" a composition or compound may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention. One preferred therapeutic agent is (+)BAY K8644 (Methyl 2,6-dimethyl-5-nitro-4-[2-(trifluoromethyl)phenyl]-1,4-dihydropyridine-3-carboxylate).

A "pharmacologically active amount" of a compound as used herein is a predetermined amount calculated to achieve a response from a biochemical pathway subjected to the compound. The response may be evidenced by spectroscopic measurement, isotopic labeling, or any other method conventionally used to investigate biochemical mechanisms. A "therapeutically effective amount" or "effective amount" of a therapeutic is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the therapeutics of the invention may be used to provide improvement in any of the conditions described. It is also contemplated that the therapeutics described herein may be administered to healthy subjects or individuals not exhibiting symptoms but who may be at risk of developing a particular disorder. The specific dose of a therapeutic agent administered according to this invention to obtain therapeutic and/or prophylactic effects will, of course, be determined by the particular circumstances surrounding the case, including, for example, the therapeutic agent administered, the route of administration, and the condition being treated. However, it will be understood that the chosen dosage ranges are not intended to limit the scope of the invention in any way. A therapeutically effective amount of a therapeutic of this invention is typically an amount such that when it is administered in a physiologically tolerable excipient composition, it is sufficient to achieve an effective systemic concentration or local concentration in the tissue.

The terms "treat," "treated," "treating," and "treatment" as used herein refer to both therapeutic and prophylactic or preventative measures, wherein the object is to prevent or slow down (lessen) an undesired physiological condition, disorder, or disease, or to obtain beneficial or desired clinical results in a person or animal. The present invention described herein fulfills an unmet need for new pharmacological strategies to treat tumors via anti-tumoral immune responses.

The present invention described herein fulfills an unmet need for new pharmacological strategies to treat tumors via anti-tumoral immune responses.

Immune checkpoints are regulators of the immune system. These pathways are crucial for self-tolerance, which prevents the immune system from attacking cells indiscriminately. However, some cancers can protect themselves from attack by stimulating immune checkpoint targets. Inhibitory checkpoint molecules are targets for cancer immunotherapy due to their potential for use in multiple types of cancers.

Anti-CTLA-4 and anti-PD-1 therapies are currently the approved checkpoint inhibitors which block CTLA4 and PD-1 and PD-L1:

Two immunotherapeutic strategies are being used in the clinic: one targets cytotoxic T lymphocyte-associated protein (CTLA)-4; see Twyman-Saint Victor, C., A. J. Rech, A. Maity, R. Rengan, K. E. Pauken, E. Stelekati, J. L. Benci, B. Xu, H. Dada, P. M. Odorizzi, R. S. Herati, K. D. Mansfield, D. Patsch, R. K. Amaravadi, L. M. Schuchter, H. Ishwaran, R. Mick, D. A. Pryma, X. Xu, M. D. Feldman, T. C. Gangadhar, S. M. Hahn, E. J. Wherry, R. H. Vonderheide and A. J. Minn, "Radiation and dual checkpoint blockade activate non-redundant immune mechanisms in cancer." Nature 520(7547): 373-377(2015), incorporated herein as a reference; and the other targets the programmed cell death 1(PD-1)/PD ligand 1 (PD-L1) pathway.

Although immune checkpoint blockers have yielded significant clinical benefits in patients with different malignancies, the efficacy of these therapies is still limited.

The current invention discloses the identification, characterization and manipulation of novel targets to promote anti-tumoral immune responses and to improve the anti-tumor efficacy of anti-CTLA-4 and anti-PD-1 therapies.

In this context, Ion channels have recently emerged as new checkpoints in tumor-specific T cells. Our team has shown that inflammasome activation by pharmacologically targeting Tmem176b improves the anti-tumor efficacy of anti-CTLA-4 and anti-PD-1 therapies see Segovia et al. "Cancer Cell (in press) also incorporated herein as a reference.

Specifically, Segovia discloses that disruption of transmembrane protein 176B (Tmem176B) contributes to CD8+ T cell-mediated tumor growth inhibition by unleashing inflammasome activation. This pharmacological approach manipulates expression of the Tmem176b gene, also known as TORID (TOlerance Related and InduceD), to treat tumors. The present invention is a method of inhibiting TORID to impair tumor growth that includes exposing TORID to a pharmacologically active amount of an ion channel modulator.

Additionally, a previous patent application by our group, WO2018203262A1 titled: "Immune-responsive methods of treating tumors", disclosed a new pharmacological strategy for the treatment of tumors based on anti-tumoral immune responses. Specifically, WO2018203262A1 discloses a method of inhibiting TORID to impair tumor growth that includes exposing TORID to a pharmacologically active amount of an ion channel modulator, while the ion channel modulator is a molecule for which different isomers can act as activator or inhibitor of voltage-gated calcium channels. In one embodiment, the calcium channel agonist is (−)BAY K8644. Administering (+)BAY K8644 inhibited TORID activity and elicits increased inflammasome (NLRP3) expression, which results in a higher rate of survival in two tumor types in anti-PD-1 resistant mice.

Current invention discloses identifying several compounds, which increase inflammasome (NLRP3) activation, as well as—inhibit TORID activity, thereby are candidates to improve efficacy of immune check point inhibitors (as a second therapeutic agent) in cancer treatment The identification method of these compositions is performed by combined two in vitro tests:

a. Triggering inflammasome activation; and
b. inhibiting TORID-dependent ion flux More specifically, the current invention discloses a combination of two in vitro assays, to identify and screen for compounds which will improve the anti-tumor efficacy of anti-CTLA-4 and anti-PD-1 therapies. Compounds which show both triggering inflammasome activation and inhibiting TORID-dependent ion flux are selected for the improvement of the anti-tumor efficacy of anti-CTLA-4 and anti-PD-1 (checkpoint) therapies.

The method for identification of new compounds to improve the anti-tumor efficacy of anti-CTLA-4 and anti-PD-1 therapies, is performed by assaying two in vitro assays and combining data resulted of these two assays:

a. Triggering inflammasome activation: Mouse bone marrow-derived dendritic cells (BMDCs) are treated with LPS and ATP to trigger NLRP3 inflammasome activation in the presence of vehicle control (DMSO) or the indicated ion channels modulators. IL-1β is measured in the culture supernatant by ELISA.
  [IL-1β was used to measure the degree of inflammasome activation]

b. Inhibiting TORID-dependent ion flux: CHO-7 cells were transfected with TORID-1 and TORID-2 plasmids. Cells were then loaded with the $Na^+$-sensitive fluorescent dye-ANG-2-. ANG-2 mean fluorescence intensity (MFI) subtracting in each condition the MFI obtained in Na+-free buffer substituted with NMDG+ is shown. Cells left untreated or treated with the indicated drugs were studied
  [MFI was used to measure the degree of inhibition of TORID-dependent ion flux. The change in fluorescent intensity shown indicates that a tested compound inhibits TORID activity]

In one embodiment, the ion channel modulator is a molecule that can act as activator or inhibitor of voltage-gated calcium channels. In another embodiment, the ion channel modulator can inhibit TORID-dependent ion fluxes (FIGS. 1A, 1B, 1C, 1D, 2A, 2B, 2C). In another embodiment, the TORID inhibitor can be either of the following compounds: Aconitine, Lidocaine, Procainamide, Propafenone, QX-314, SDZ201106, Veratridine or Phenytoin (FIGS. 1A, 1B, 1C, 1D, 2A, 2B, 2C). In another embodiment, the method of treating the tumor includes administering one or more second therapeutic agents to a patient in need thereof. The ion channel modulators are presented in FIGS. 3A and 3B.

In one embodiment, the second therapeutic agent is administered concurrently with the ion channel ligand. In one embodiment, the second therapeutic agent is administered sequentially with the ion channel ligand. In one embodiment, the second therapeutic agent is an anti-CTLA4 antibody or an anti-PD-1/PD-L1 antibody. In one embodiment, the second therapeutic agent is radiation therapy. In one embodiment, the second therapeutic agent is an anti-CTLA4 antibody or an anti-PD-1/PD-L1 antibody and radiation therapy.

Examples

Reference is now made to FIGS. 1A, 1B, 1C, and 1D presenting compounds that enhance NLRP3 inflammasome activation and inhibit TORID activity according to one embodiment of the invention (Lidocaine, Aconitine, Procainamide, Propafenone).

Figure 1A:
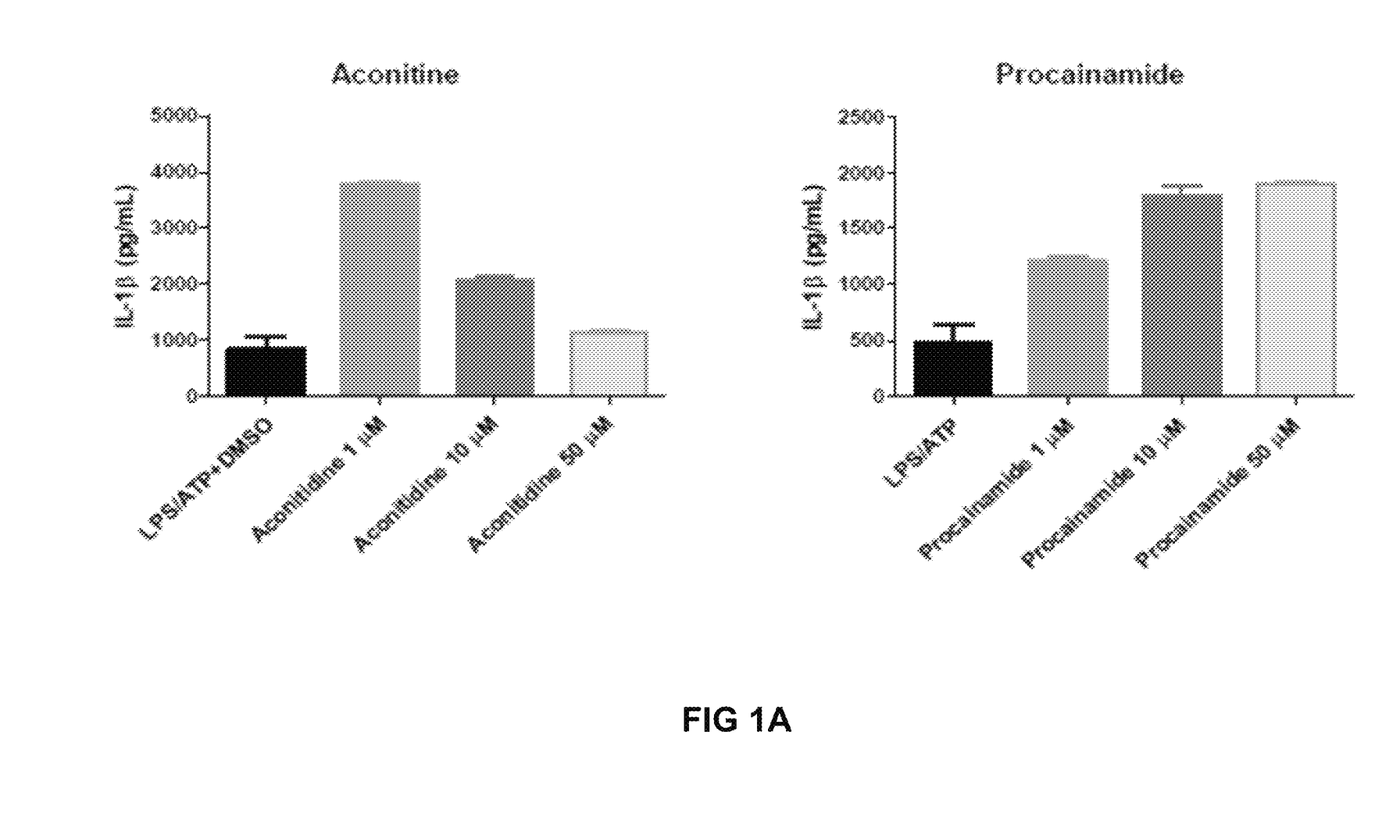
FIG. 1A depicts IL-1β activity measured in the culture supernatant by ELISA, for the compounds: Aconitine and Procainamide.
Figure 1B:
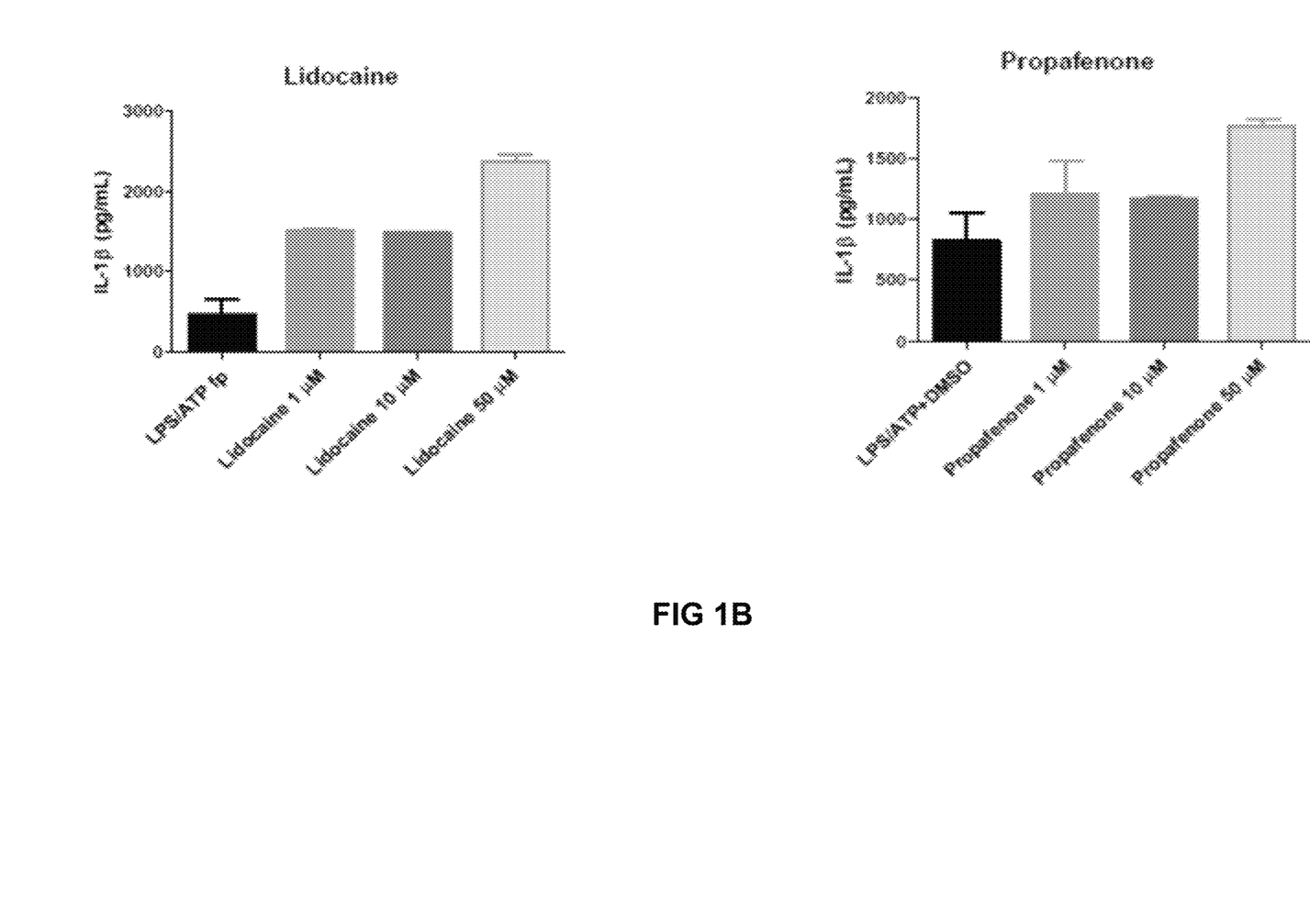
FIG. 1B depicts IL-1β activity measured in the culture supernatant by ELISA, for the compounds: Lidocaine and Propafenone.

A Mouse bone marrow-derived dendritic cells (BMDCs) were treated with LPS (0.25 μg/ml for 3 hr) and ATP (0.5 mM) to trigger NLRP3 inflammasome activation in the presence of vehicle control (DMSO) or the indicated ion channels modulators. IL-1β was measured in the culture supernatant by ELISA.

Figure 1C:
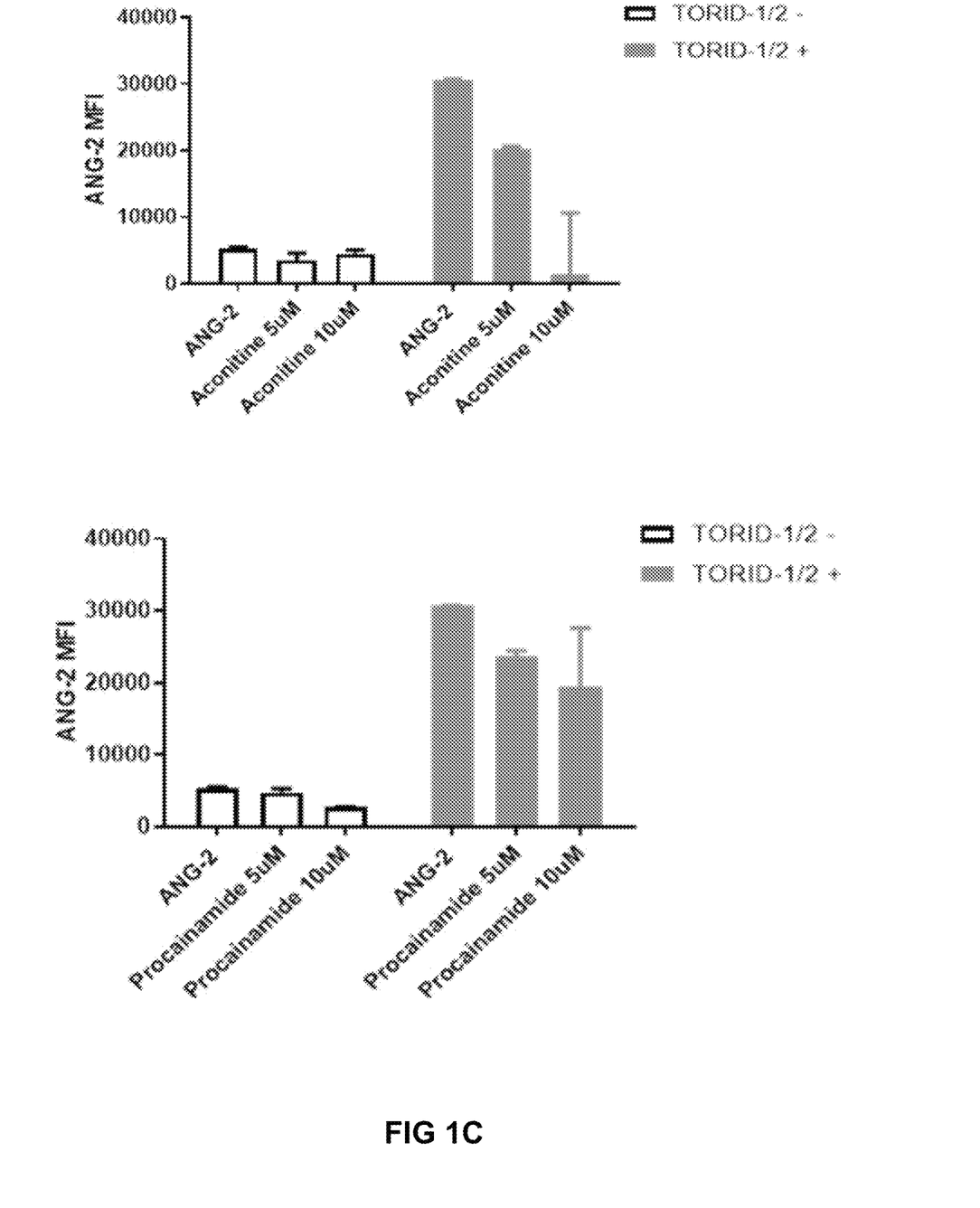
FIG. 1C depicts the Na+-sensitive fluorescent dye Asante NaTRIUM Green 2 (ANG-2) mean fluorescence intensity (MFI), for the compounds: Aconitine and Procainamide.
Figure 1D:
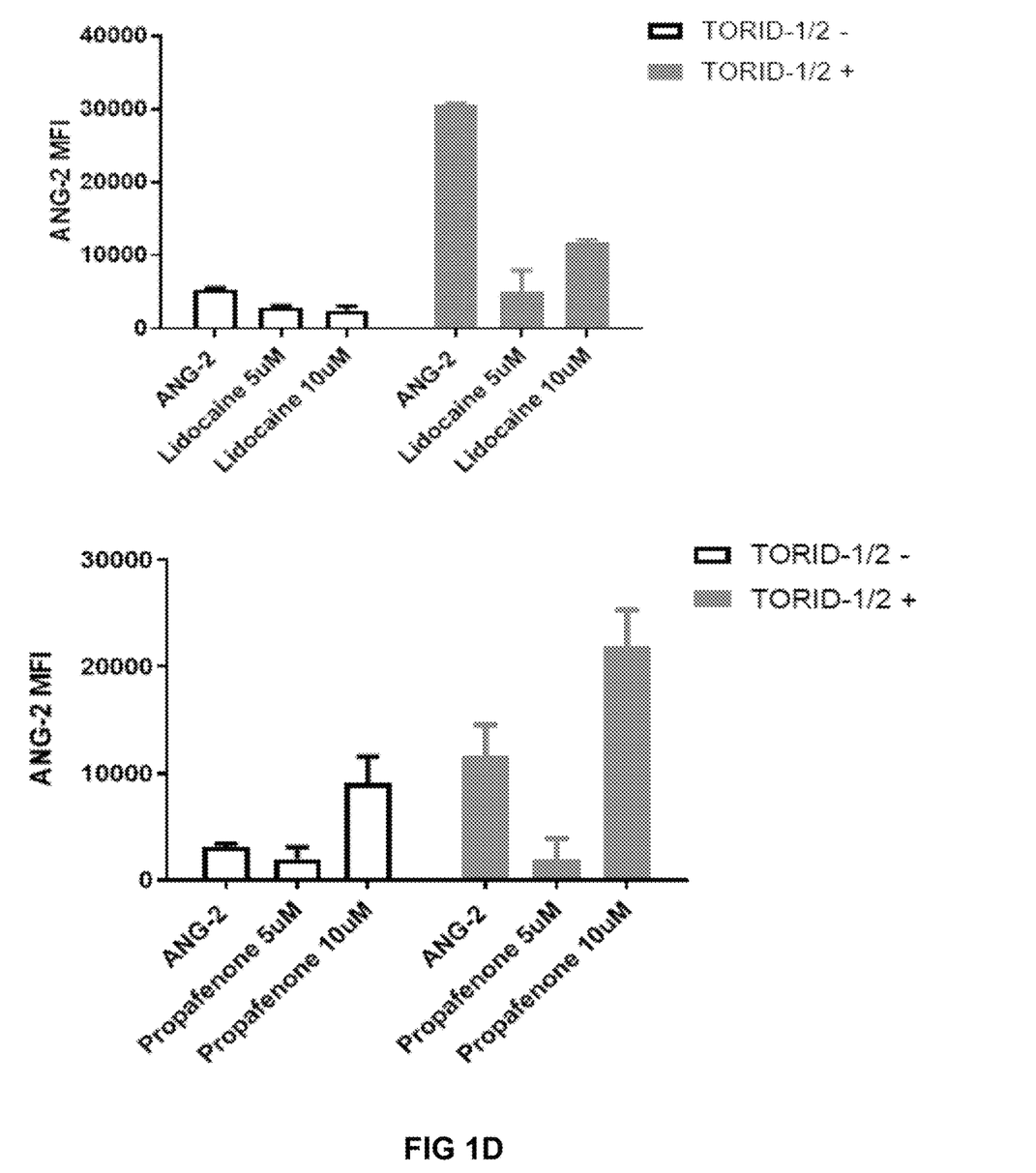
FIG. 1D depicts the Na+-sensitive fluorescent dye Asante NaTRIUM Green 2 (ANG-2) mean fluorescence intensity (MFI), for the compounds Lidocaine and Propafenone.

B CHO-7 cells were transfected with Tmem176b (TORID-1) and Tmem176a (TORID-2)-mcherry-coding pSecTag2B plasmids. Cells were then loaded with the $Na^+$-sensitive fluorescent dye Asante NaTRIUM Green 2 (ANG-2). ANG-2 mean fluorescence intensity (MFI) subtracting in each condition the MFI obtained in $Na^+$-free buffer substituted with $NMDG^+$ is shown. Cells left untreated or treated with the indicated drugs were studied.

Figure 2A:
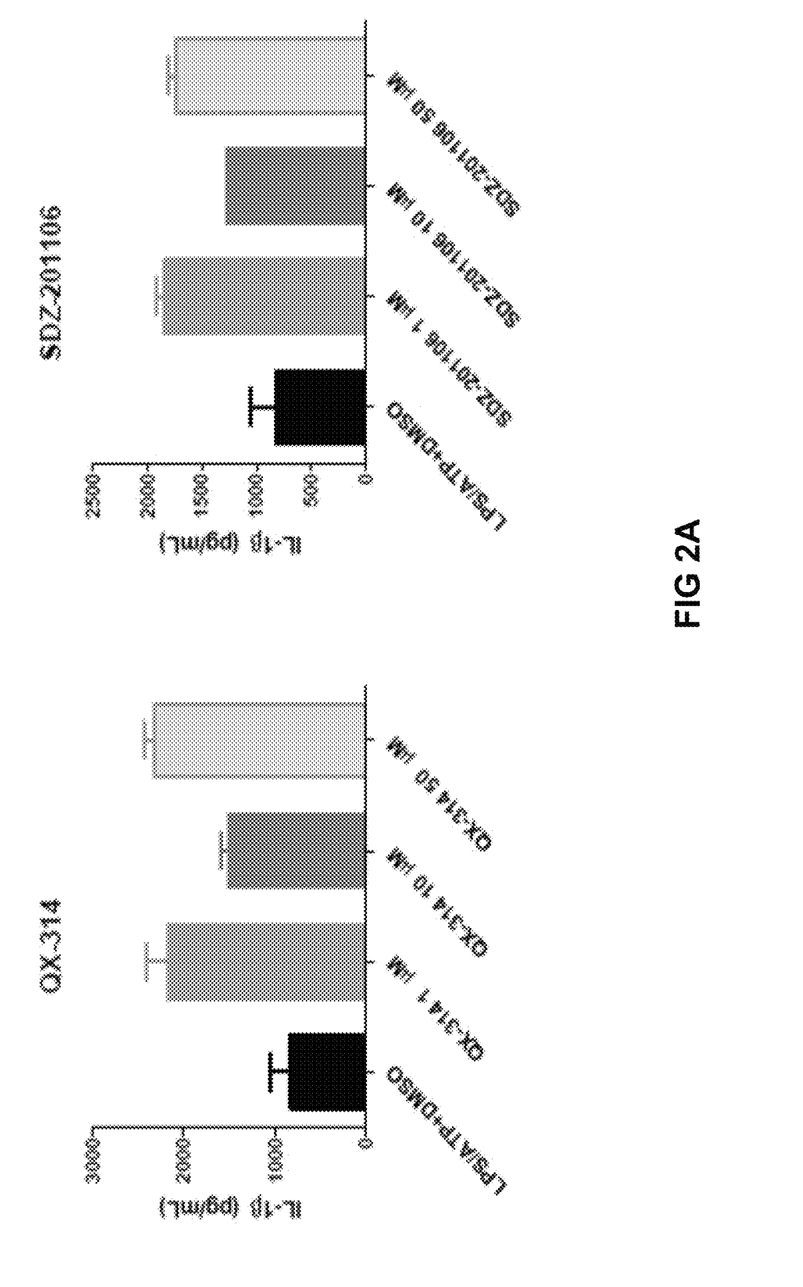
FIG. 2A depicts the activity of the compounds: QX-314, SDZ-201106, Veratridine and Phenytoin.
Figure 2B:
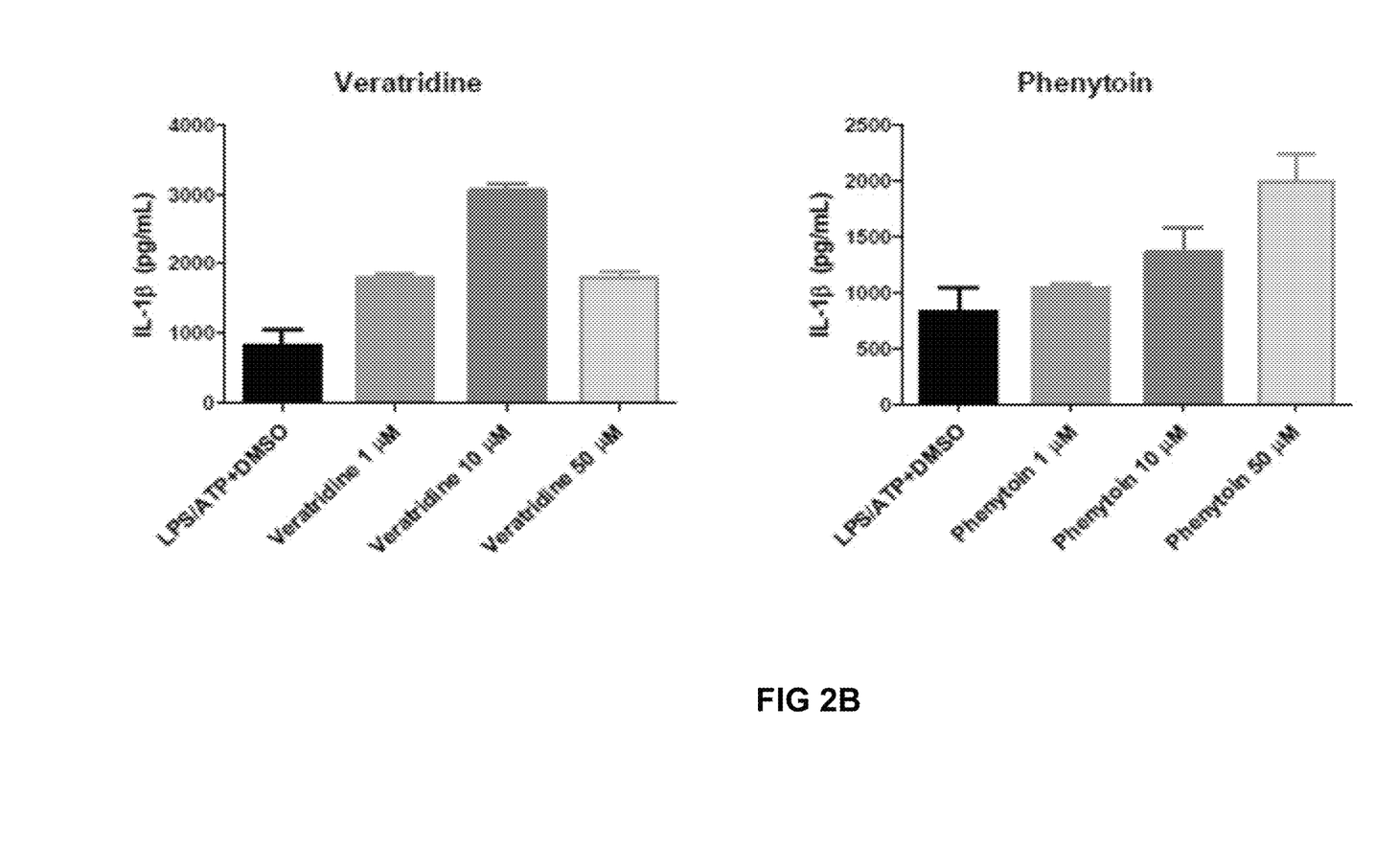
FIG. 2B depicts IL-1β activity measured in the culture supernatant by ELISA.
Figure 2C:
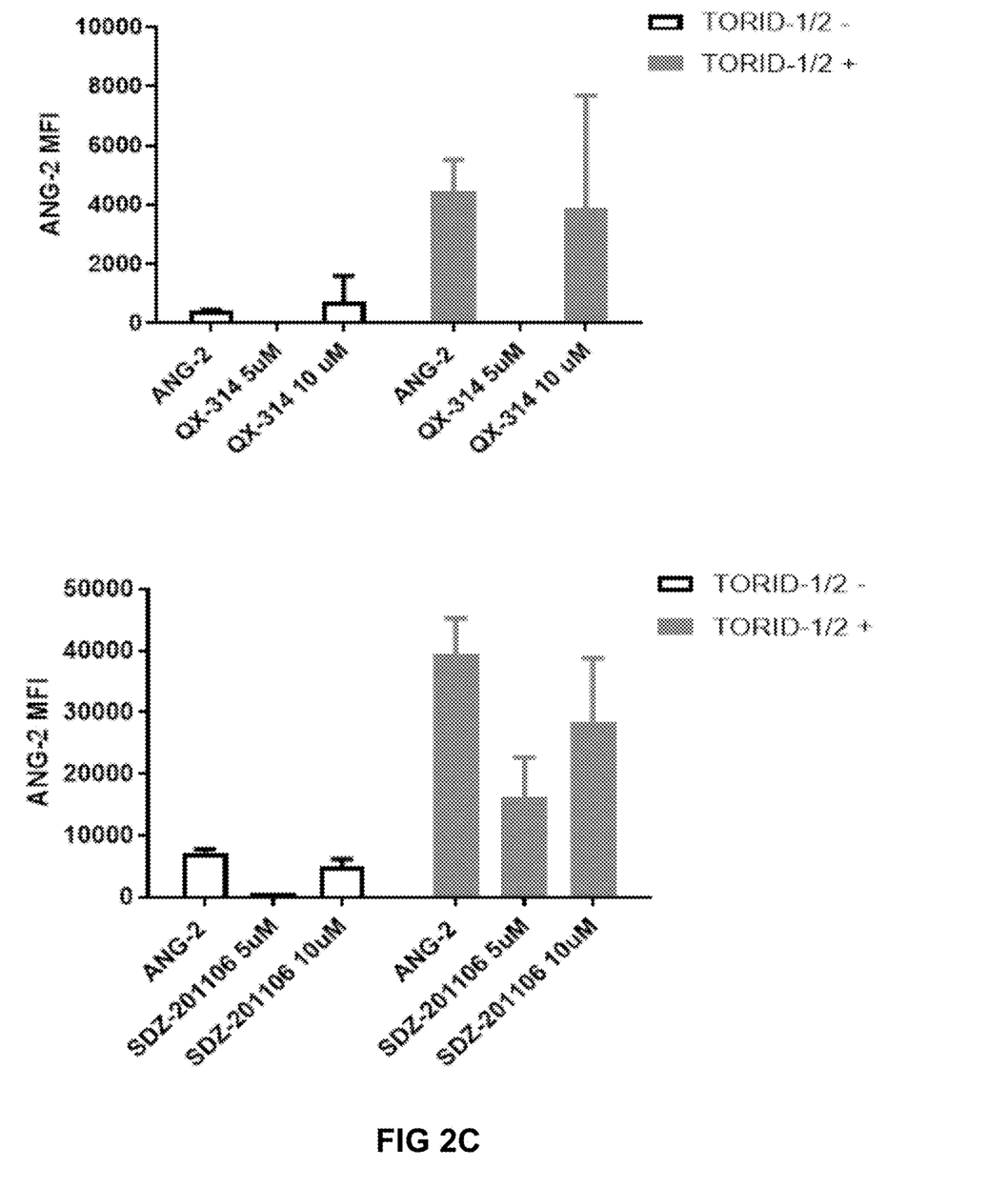
FIG. 2C depicts ANG-2 mean fluorescence intensity (MFI)
Figure 3A:
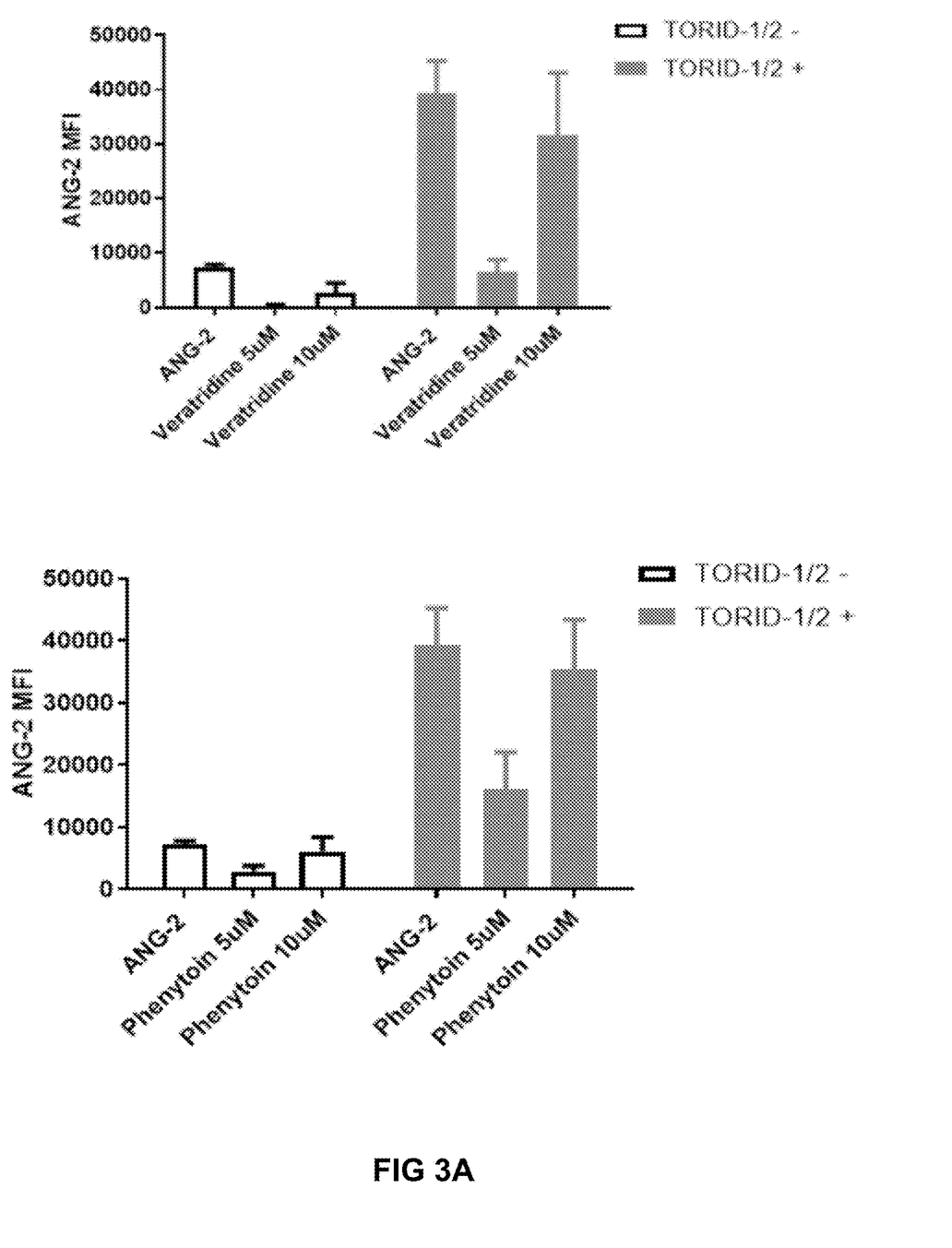
FIGS. 3A and 3B depicts the chemical structures of the compounds.
Figure 3B:
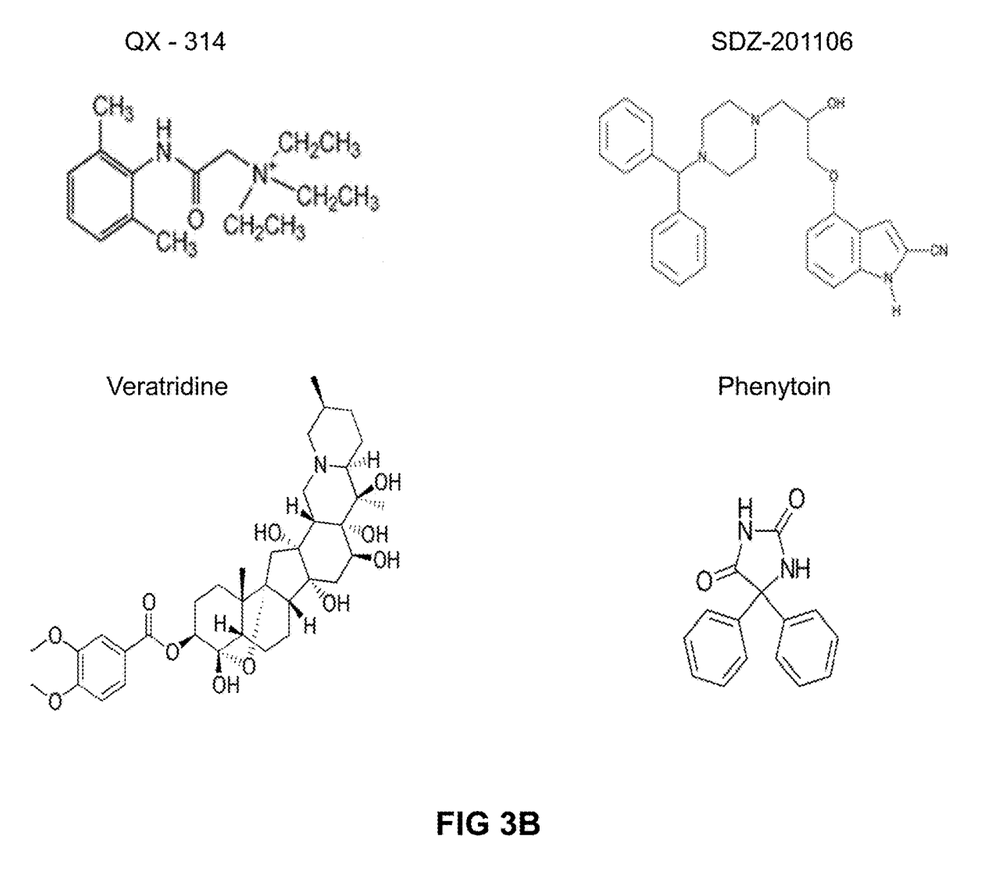

Reference is now made to FIGS. 2A, 2B, 2C, presenting compounds that enhance NLRP3 inflammasome activation and do not inhibit TORID activity.

A Mouse bone marrow-derived dendritic cells (BMDCs) were treated with LPS (0.25 μg/ml for 3 hr) and ATP (0.5 mM) to trigger NLRP3 inflammasome activation in the presence of vehicle control (DMSO) or the indicated ion channels modulators. IL-1β was measured in the culture supernatant by ELISA.

B CHO-7 cells were transfected with Tmem176b (TORID-1) and Tmem176a (TORID-2)-mcherry-coding pSecTag2B plasmids. Cells were then loaded with the $Na^+$-sensitive fluorescent dye Asante NaTRIUM Green 2 (ANG-2). ANG-2 mean fluorescence intensity (MFI) subtracting in each condition the MFI obtained in $Na^+$-free buffer substituted with $NMDG^+$ is shown. Cells left untreated or treated with the indicated drugs were studied.

The results show several molecules, which have been identified by the screening based on a combination of two in vitro assays. These compounds which showed both triggering inflammasome activation and inhibiting TORID-dependent ion flux are selected for the improvement of the anti-tumor efficacy of anti-CTLA-4 and anti-PD-1 (checkpoint) therapies.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A composition of use as a second therapeutic agent, to improve the efficacy of a first therapeutic agent which is an immune checkpoint blocker, wherein said composition is configured to trigger inflammasome activation and to inhibit TORID-dependent ion fluxes; further wherein said composition is selected from a group consisting of Aconitine, Lidocaine, Procainamide, Propafenone and any combination thereof.

2. The method of claim 1, wherein one or more second therapeutic agents are administrable either concurrently or sequentially to a patient in need.

\* \* \* \* \*